US012329544B2

United States Patent
Qiao et al.

(10) Patent No.: US 12,329,544 B2
(45) Date of Patent: Jun. 17, 2025

(54) METHOD AND SYSTEM FOR OPTIMIZING FILTER SETTINGS OF AN IMPLANTABLE MEDICAL DEVICE

(71) Applicant: Pacesetter, Inc., Sylmar, CA (US)

(72) Inventors: Yun Qiao, Sunnyvale, CA (US); Fady Dawoud, Studio City, CA (US); Wenwen Li, San Jose, CA (US); Chaoyi Kang, Northridge, CA (US)

(73) Assignee: Pacesetter, Inc., Sylmar (CA)

( * ) Notice: Subject to any disclaimer, the term of this patent is extended or adjusted under 35 U.S.C. 154(b) by 402 days.

(21) Appl. No.: 17/720,748

(22) Filed: Apr. 14, 2022

(65) Prior Publication Data

US 2022/0409143 A1    Dec. 29, 2022

Related U.S. Application Data

(60) Provisional application No. 63/215,532, filed on Jun. 28, 2021.

(51) Int. Cl.
*A61B 5/00* (2006.01)
*A61B 5/318* (2021.01)

(52) U.S. Cl.
CPC .............. *A61B 5/725* (2013.01); *A61B 5/318* (2021.01); *A61B 5/686* (2013.01)

(58) Field of Classification Search
None
See application file for complete search history.

(56) References Cited

U.S. PATENT DOCUMENTS

| | | | |
|---|---|---|---|
| 7,294,109 B2 | 11/2007 | Lovett et al. | |
| 10,111,600 B2 | 10/2018 | Ox et al. | |
| 10,512,784 B2 | 12/2019 | Hahn et al. | |
| 10,783,223 B2 | 9/2020 | Andersen | |
| 2003/0050563 A1 | 3/2003 | Suribhotla et al. | |
| 2015/0238091 A1* | 8/2015 | Iyer | A61B 5/0095 600/407 |
| 2017/0156617 A1 | 6/2017 | Allavatam et al. | |
| 2017/0172426 A1 | 6/2017 | Oz et al. | |
| 2019/0114393 A1* | 4/2019 | Andersen | A61B 5/686 |
| 2020/0376284 A1 | 12/2020 | Gill et al. | |
| 2021/0113135 A1 | 4/2021 | Allavatam et al. | |

OTHER PUBLICATIONS

Extended European Search Report for corresponding EP Application No. 22168927 dated Sep. 29, 2022 (8 pages).
Tereshchenko et al. "Frequency Content and Characteristics of Ventricular Conduction" HSP Public Access; Nov. 2016 (9 pages).

* cited by examiner

*Primary Examiner* — Sana Sahand
(74) *Attorney, Agent, or Firm* — Dean D. Small; The Small Patent Law Group, LLC

(57) ABSTRACT

A system and a method include an implantable medical device (IMD) having one or more inputs configured to receive one or more sensed signals from one or more electrodes. A plurality of filters are configured to filter the one or more sensed signals and output a plurality of filtered signals. Memory is configured to store program instructions. A processor, when executing the program instructions, is configured to receive the plurality of filtered signals, and analyze the plurality of filtered signals to determine a desired one of the plurality of filters.

21 Claims, 7 Drawing Sheets

METHOD AND SYSTEM FOR OPTIMIZING FILTER SETTINGS OF AN IMPLANTABLE MEDICAL DEVICE

RELATED APPLICATION

The present application claims priority to U.S. Provisional Application No. 63/215,532, Titled "METHOD AND SYSTEM FOR OPTIMIZING FILTER SETTINGS OF AN IMPLANTABLE MEDICAL DEVICE" which was filed on 28 Jun. 2021, the complete subject matter of which is expressly incorporated herein by reference in their entirety.

Embodiments herein relate generally to implantable medical devices, and more particularly to methods and systems for optimizing filter settings of implantable medical devices.

Implantable medical devices (IMD) include pacemakers, cardioverters, cardiac rhythm management devices, defibrillators, whether lead-based or leadless, or the like. Each product is implanted in an individual to treat heart ailments and conditions through an electronically operated device. Many implantable medical products store a large amount of biological data from sensors.

A variety of sensors, the most basic being electrical sensing of the heart, are constantly being monitored and stored in memory. Noise sources such as alternating current (AC) voltage sources can introduce noise that is close or in the band of frequencies that are of interest to signals that are being monitored. Such noise can cause incorrect signal interpretation and interfere with the general operation of the IMDs.

Filters are utilized to block this extrinsic noise from interfering with signal interpretation performed by the IMD. Typically, accurate and reliable R-wave sensing relies on appropriate filtering of electrograms (EGMs).

In an IMD such as a non-vascular implantable cardioverter-defibrillator (NV-ICD), a sensed cardiac signal is similar to an electrocardiogram in terms of frequency content and signal morphology because the sensing electrodes are located outside of the heart. Numerous studies have demonstrated that the most information-rich frequency range of frequencies varies from patient to patient due to differences in electrophysiological properties and potential disease conditions. Additionally, the frequency content and morphology of signals could change over time in an individual due to cardiac remodeling or disease progression.

SUMMARY

A need exists for optimizing filter settings of an IMD of an individual based on individual-specific electrocardiogram signals, in order to increase the ability of the IMD to attenuate unwanted signals (for example, P- and T-waves) while preserving R-wave amplitude. Further, a need exists for in IMD exhibiting increased accuracy and robustness of R-wave sensing, which facilitates normal operation of downstream arrhythmia detection.

With those needs in mind, certain embodiments provide a system including an implantable medical device (IMD) having one or more inputs configured to receive one or more sensed signals from one or more electrodes. A plurality of filters are configured to filter the one or more sensed signals and output a plurality of filtered signals. Memory is configured to store program instructions. A processor, when executing the program instructions, is configured to receive the plurality of filtered signals, and analyze the plurality of filtered signals to determine a desired one of the plurality of filters.

In at least one example, the one or more sensed signals include one or more sensed electrogram (EGM) signals.

In at least one example, each of the plurality of filters is configured as a low pass filter, a high pass filter, a band pass filter, or a band stop filter.

In at least one example, the one or more sensed signals are collected from an individual during one or more of sinus rhythm (SR), ventricular tachycardia (VT), or ventricular fibrillation (VF).

In at least one example, the one or more sensed signals are received by the one or more inputs when the IMD is implanted into an individual.

As an example, the plurality of filters can include a 6-30 Hz narrowband filter, an 8-30 Hz narrowband filter, a 10-30 Hz narrowband filter, and a 12-30 Hz narrowband filter.

In at least one embodiment, the processor is configured to determine the desired one of the plurality of filters based on one or more criteria that differentiates among the plurality of filter signals. For example, the one or more criteria are determined by the processor via scoring. As a further example, the processor is configured to score the plurality of filter signals through analysis of an original R-wave amplitude ($R_{ori}$), filtered R-wave amplitude ($R_{filt}$), filtered T-wave amplitude ($T_{filt}$), original R-wave amplitude during VT ($VT_{ori}$), and filtered R-wave amplitude during VT ($VT_{filt}$) to quantify a performance of each of the plurality of filters in accordance with the following equation:

$$\text{score} = w1 \times \frac{R_{filt}}{R_{ori}} + w2 \times \frac{VT_{filt}}{VT_{ori}} + w3 \times \left(1 - \frac{T_{filt}}{R_{filt}}\right)$$

where w1, w2, and w3 are weights.

In at least one example, the processor is further configured to program the IMD to use the desired one of the plurality of filters and refrain from using the other of the plurality of filters.

In at least one example, the processor is further configured to periodically analyze the plurality of filtered signals based on one or more triggering events. For example, the one or more triggering events can include one or both of a predetermined time period or an R-wave amplitude below a predetermined threshold.

Certain embodiments of the present disclosure provide a computer implemented method, under control of one or more processors, where the one or more processors are configured with specific executable instructions, the computer implemented method comprising: receiving, by one or more inputs, one or more sensed signals from one or more electrodes; filtering, by a plurality of filters, the one or more sensed signals; receiving the plurality of filtered signals from the plurality of filters; analyzing the plurality of filtered signals; and determining, via said analyzing, a desired one of the plurality of filters.

DETAILED DESCRIPTION

Figure 1A:
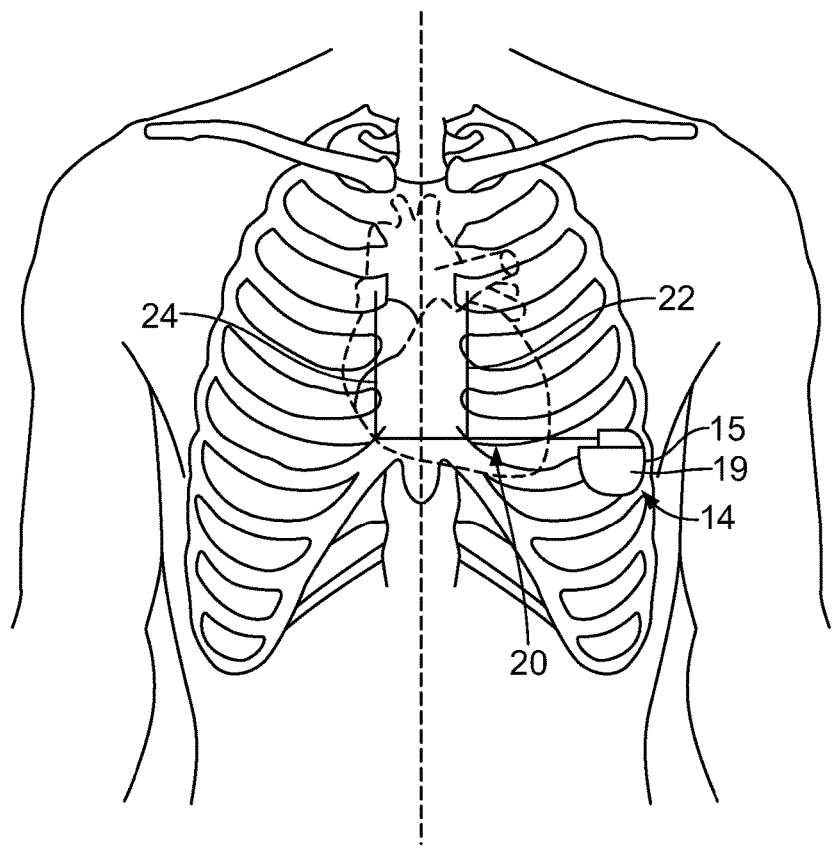
FIG. 1A illustrates a graphical representation of a subcutaneous implantable medical system that is configured to implement the methods described herein and apply therapy to a heart.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "adaptive", as used in connection with a sensitivity profile, sensitivity limit, sensitivity level or other sensing parameters, refers to an ability of the processes herein to modify the value of sensitivity and/or sensing parameters or thresholds based on features within the CA signals. The sensitivity profile parameters may include refractory period, start sensitivity, decay delay, sensitivity limit, slope of sensitivity decay, etc.

The terms "abnormal," "arrhythmic" and "arrhythmia" are used to refer to events, features, and characteristics of, or appropriate to, an un-healthy or abnormal functioning of the heart. Non-limiting examples of arrhythmias include ventricular fibrillation (VF), ventricular tachycardia (VT), atrial fibrillation (AF) and atrial tachycardia (AT).

The terms "cardiac activity signal", "cardiac activity signals", "CA signal" and "CA signals" (collectively "CA signals") are used interchangeably throughout to refer to measured signals indicative of cardiac activity by a region or chamber of interest. For example, the CA signals may be indicative of impedance, electrical or mechanical activity by one or more chambers (e.g., left or right ventricle, left or right atrium) of the heart and/or by a local region within the heart (e.g., impedance, electrical or mechanical activity at the AV node, along the septal wall, within the left or right bundle branch, within the purkinje fibers). The cardiac activity may be normal/healthy or abnormal/arrhythmic. An example of CA signals includes electrocardiogram signals. Electrical based CA signals refer to an analog or digital electrical signal recorded by two or more electrodes, where the electrical signals are indicative of cardiac activity. Heart sound (HS) based CA signals refer to signals output by a heart sound sensor such as an accelerometer, where the HS based CA signals are indicative of one or more of the S1, S2, S3 and/or S4 heart sounds. Impedance based CA signals refer to impedance measurements recorded along an impedance vector between two or more electrodes, where the impedance measurements are indicative of cardiac activity.

The term "COI" refers to a character of interest. Nonlimiting examples of characters of interest within CA signals include an R-wave, P-wave, T-wave, S1 heart sound, S2 heart sound, S3 heart sound or S4 heart sound. A character of interest may correspond to a peak, average, mean or other statistical parameter of an individual R, P, R or T-wave peak, S1 heart sound, S2 heart sound, S3 heart sound or S4 heart sound and the like.

The terms "beat" and "cardiac event" are used interchangeably and refer to both normal or abnormal events.

The terms "normal", "sinus", "normal sinus" and "SR" are used to refer to events, features, and characteristics of, or appropriate to, a heart's healthy or normal functioning.

The term "real-time" refers to a time frame contemporaneous with a normal or abnormal episode occurrences. For example, a real-time process or operation would occur during or immediately after (e.g., within minutes or seconds after) a cardiac event, a series of cardiac events, an arrhythmia episode, and the like.

The term "noise" refers to any and all disturbances in a communication signal. The communication may be electronic, wireless, over the air, through a cellular network, or the like. The noise may include any random error, deflection, etc. from the intended signal. Noise can be measured in units for frequency, energy, or the like.

The term "upper cut-off frequency" refers to the maximum frequency that is filtered by a filtering device such as a band-stop filter. Specifically, a band-stop filter can filter noise in a range, such as 5 Hz, 10 Hz, etc. where the maximum frequency is the upper cut-off frequency. In this manner, if a band-stop filter filters noise in a 10 Hz range between 55 Hz and 65 Hz, 65 Hz is considered the upper cut-off frequency. If a band pass filter filters noise in a 4 Hz range between 48 Hz and 52 Hz, 52 Hz is the upper cut-off frequency.

The term "lower cut-off frequency" refers to refers to the minimum frequency that is filtered by a filtering device such as a band-stop filter. Specifically, a band-stop filter can filter noise in a range, such as 5 Hz, 10 Hz, etc. where the minimum frequency is the lower cut-off frequency. In this manner, if a band-stop filter filters noise in a 10 Hz range between 55 Hz and 65 Hz, 55 Hz is considered the lower cut-off frequency. If a band-stop filter filters noise in a 4 Hz range between 48 Hz and 52 Hz, 48 Hz is the lower cut-off frequency.

The term "filter parameters" refers to the frequency at which a filtering device, such as a band-stop filter, filters noise. The filter parameters can include a specific frequency at which noise is being filtered, or a range or band of frequencies.

The term "measured impedance" refers to intracardiac and/or intrathoracic impedance measurements directly measured from a combination of electrodes positioned within the heart, proximate to the heart and/or within the chest wall.

The term "subcutaneous" shall mean below the skin, but not intravenous. For example, a subcutaneous electrode/lead does not include an electrode/lead located in a chamber of the heart, in a vein on the heart, or in the lateral or posterior branches of the coronary sinus.

The term "marker" refers to data and/or information identified from CA signals that may be presented as graphical and/or numeric indicia indicative of one or more features within the CA signals and/or indicative of one or more episodes exhibited by the cardiac events. Markers may be superimposed upon CA signals or presented proximate to, and temporally aligned with, CA signals. Non-limiting examples of markers may include R-wave markers, noise markers, activity markers, interval markers, refractory markers, P-wave markers, T-wave markers, PVC markers, sinus rhythm markers, AF markers and other arrhythmia markers. As a further non-limiting example, basic event markers may include "AF entry" to indicate a beginning of an AF event, "in AF" to indicate that AF is ongoing, "AF exit" to indicate that AF has terminated, "T" to indicate a tachycardia beat, "B" to indicate a bradycardia beat, "A" to indicate an asystole beat, "VS" to indicate a regular sinus beat, "Tachy" to indicate a tachycardia episode, "Brady" to indicate a Bradycardia episode, "Asystole" to indicate an asystole episode, "Patient activated" to indicate a patient activated episode. An activity marker may indicate activity detected by activity sensor during the CA signal. Noise markers may indicate entry/start, ongoing, recovery and exit/stop of noise. Markers may be presented as symbols, dashed lines, numeric values, thickened portions of a waveform, and the like. Markers may represent events, intervals, refractory periods, ICM activity, and other algorithm related activity. For example, interval markers, such as the R-R interval, may include a numeric value indicating the duration of the interval. The AF markers indicate atrial fibrillation rhythmic.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The abbreviations "RA", "LA", "RV" and "LV" refer to the right atrium, left atrium, right ventricle and the left ventricle respectively.

In accordance with embodiments herein, methods and systems are described for selecting (e.g., optimizing) filter settings using CA signal templates collected from a patient during sinus rhythm (SR) and VT/VF. The methods and systems automatically determine and implement the select filter settings that would result in a desired level of accuracy for R-wave sensing. The methods and systems also periodically re-evaluate and update filter settings based on various criteria to adapt to changing CA signals (e.g., changing electrogram (EGM), impedance and/or HS morphology due to cardiac remodeling and disease progression).

The methods and systems may utilize one or more sensing channels (e.g., as defined between electrodes to sense electrical or impedance-based CA signals, as defined by X, Y, Z output channels of a 3D accelerometer, etc.) of an implantable medical device, such as an insertable cardiac monitor (ICM) or a subcutaneous implantable cardio-defibrillator (S-ICD), to detect and analyze sensed events. A sensed event may correspond to the cardiac activity (CA) signals of a single beat, an R-wave, P-wave, T-wave, and the like. Embodiments determine and monitor characteristics of sensed events, such as an amplitude, a morphology of the CA signals for the single beat or sensed event, a noise floor, and one or more event intervals (e.g., P-P, P-R, R-T, and R-R intervals).

Figure 1B:
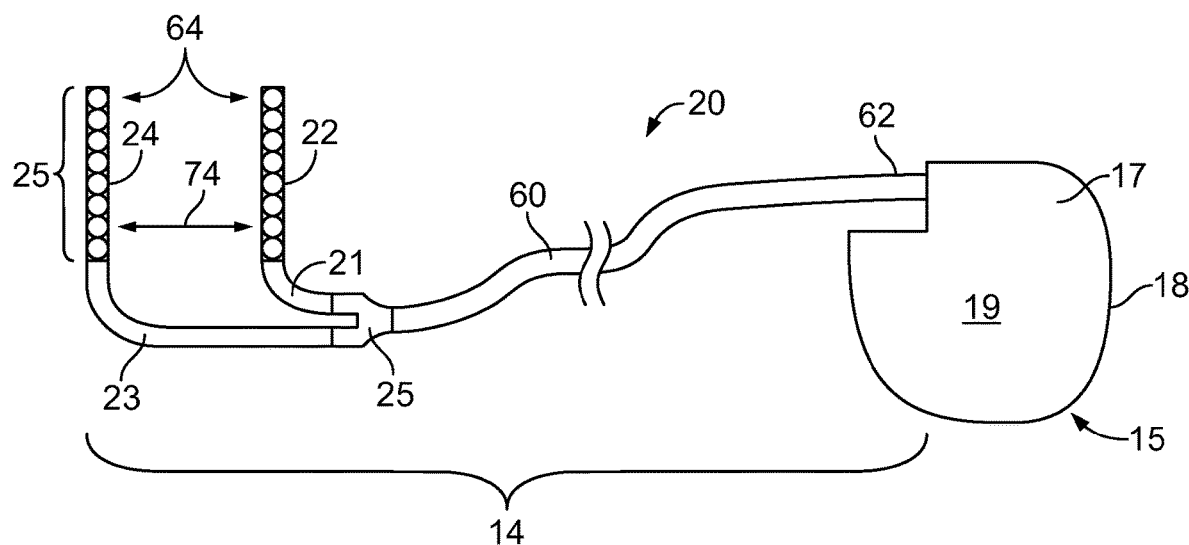
FIG. 1B illustrate a graphical representation of a subcutaneous implantable medical system that is configured to implement the methods described herein and apply therapy to a heart.

FIGS. 1A and 1B illustrate a graphical representation of a subcutaneous implantable medical system that is configured to implement the methods described herein and apply therapy to a heart. FIG. 1A illustrates a torso of a patient to show the rib cage and a general outline of the heart and greater vessels. In particular embodiments, the system may apply high voltage defibrillation shocks, as well as other general arrhythmia therapy, such as pacing therapy, cardiac resynchronization therapy (CRT), and the like. The system includes a subcutaneous implantable medical device (SIMD) 14 that is configured to be implanted in a subcutaneous area exterior to the heart. In at least one embodiment, the system is entirely or fully subcutaneous. As shown in FIG. 1A, the SIMD 14 is positioned within a lateral region, such as along the left side of the rib cage under the left arm. The SIMD 14 may be positioned relative to a vertical direction substantially aligned with the apex of the heart. The SIMD 14 is configured to deliver various arrhythmia therapies, such as defibrillation therapy, pacing therapy, anti-tachycardia pacing therapy, cardioversion therapy, and the like. It is contemplated, however, that the system may include other components. For example, alternative embodiments may include a transvenous lead or a leadless electrode in addition to the structures in FIG. 1A.

The lead 20 includes one or more electrodes 22, 24 that are used for providing electrical shock for defibrillation. Optionally, the lead 20 may include one or more sensing electrodes. A pulse generator 15 may be implanted subcutaneously and at least a portion of the lead 20 may be implanted subcutaneously. In particular embodiments, the SIMD 14 is an entirely or fully subcutaneous SIMD. The pulse generator 15 may be positioned at a lateral position or below an apex of the heart.

With reference to FIG. 1B, the lead 20 includes an elongated lead body 60 that extends from a proximal end 62 to a distal tip 64. The pulse generator 15 includes a housing 18 that is configured to be active to form a pulse-generator (PG) electrode 19. The pulse generator 15 also includes a header 17 mounted to the housing 18. The header 17 is configured to receive and be connected to the proximal end 62 of the lead body 60. The proximal end 62 may include one or more contacts (not shown) that electrically engage respective terminals (not shown) in the header 17 of the pulse generator 15.

The lead body 60 may include one or more distal branches 21, 23 that separate from a splitting connector 25, where the distal branches 21, 23 each include a corresponding one of the electrodes 22, 24, which are separated by distance 74. The splitting connector 25 may be configured in different shapes and different manners. For example, the splitting connector 25 may be formed as a Y-connector, a T-connector and the like. The splitting connector 25 may be formed as part of a monotonic unitary body structure with the lead body 60 and distal branches 21, 23.

As shown, the lead body 60 includes two distal branches 21, 23 and two electrodes 22, 24, although it is recognized that no branch, more than two branches and more than two electrodes may be provided on the lead body 60. Additionally, or alternatively, two or more separate leads 20 may be provided, with each lead 20 having a single distal segment and single electrode provided thereon. For example, the electrodes 22 and 24 may be provided on separate leads that are individually joined to the header 17. Optionally, a single lead 20 with a single electrode 22 or 24 may be used.

The electrodes 22, 24 may be referred to as first and second electrodes 22, 24 that are coupled to be electrically common with one another. The first and second electrodes 22, 24 are elongated along corresponding longitudinal axes. The first and second electrodes 22, 24 may be positioned in a dual parasternal combination extending in a common direction and spaced apart. The positioning operation may comprise positioning the first and second electrodes 22, 24 along opposite sides of the sternum, or positioning the first and second electrodes 22, 24 on a common side of the sternum. The anterior positioning operation may include positioning the second electrode proximate to a lower end of the sternum and orienting the second electrode to extend in a direction non-parallel to a direction of the first electrode, and locating the second electrode at a position, relative to a midline of the sternum, that is vertically below the first electrode. The non-parallel direction may orient a longitudinal axis of the second electrode perpendicular to a longitudinal axis of the first electrode.

With reference to FIG. 1A, the first electrode 22 may be positioned along a left side of the anterior region of the chest adjacent to the sternum. The second electrode 24 may be positioned along a right side of the anterior region of the chest adjacent to the sternum. Optionally, the leads may be provided in different configurations, different locations and different combinations other than shown.

Figure 2:
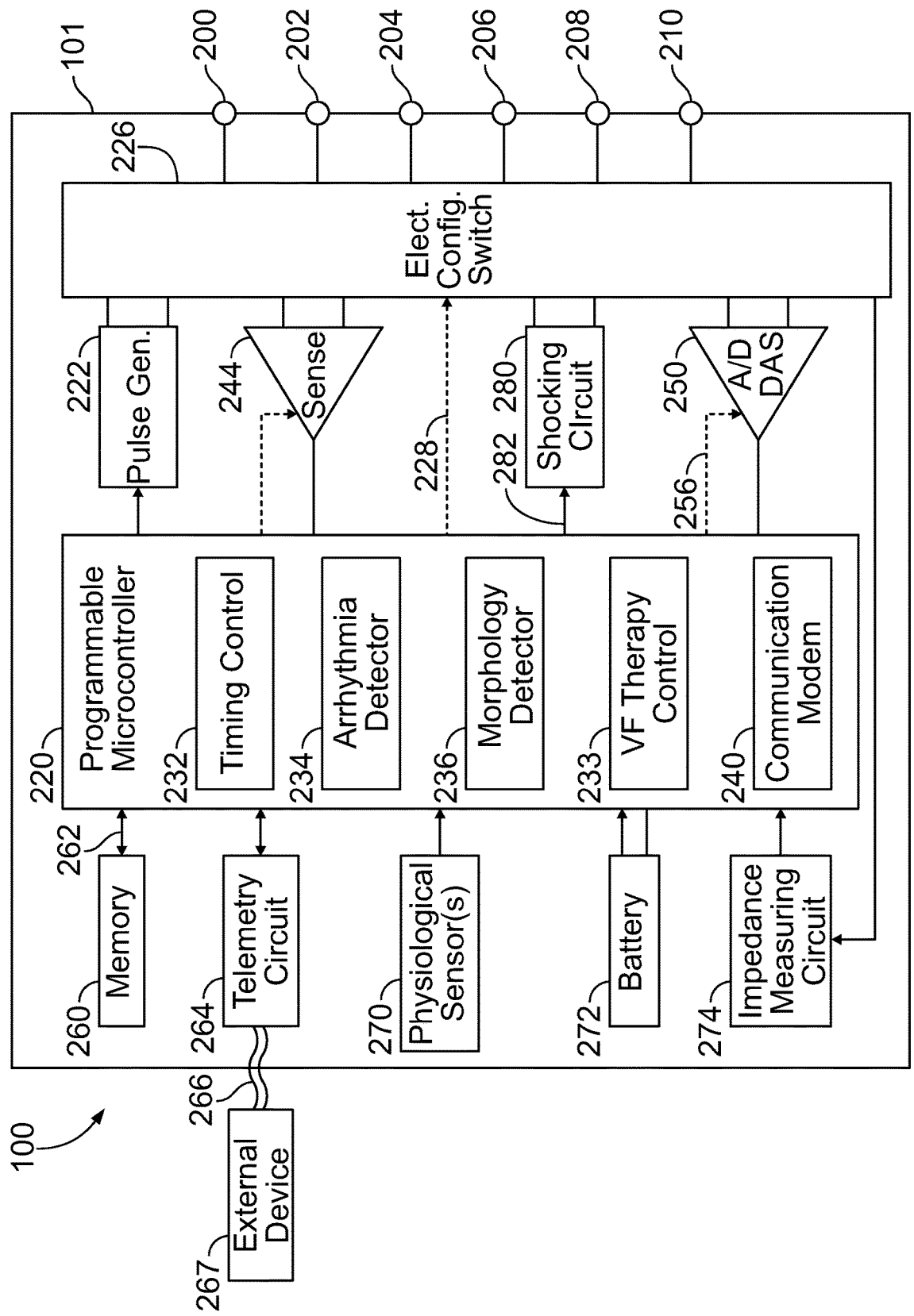
FIG. 2 illustrates a block diagram of an exemplary IMD that is implanted into the patient as part of the implantable cardiac system in accordance with embodiments herein.

FIG. 2 illustrates a block diagram of an exemplary IMD 100 that is configured to be implanted into the patient. The SIMD 14 shown in FIGS. 1A and 1B can be configured as shown in FIG. 2. The IMD 100 may treat both fast and slow arrhythmias with stimulation therapy, including cardioversion, pacing stimulation, an implantable cardioverter defibrillator, suspend tachycardia detection, tachyarrhythmia therapy, and/or the like.

The IMD 100 has a housing 101 to hold the electronic/computing components. The housing 101 (which is often referred to as the "can," "case," "encasing," or "case electrode") may be programmably selected to act as the return electrode for certain stimulus modes. The housing 101 further includes a connector (not shown) with a plurality of terminals 200-210. The terminals may be connected to electrodes that are located in various locations within and about the heart. The type and location of each electrode may vary. For example, the electrodes may include various combinations of ring, tip, coil, shocking electrodes, and the like.

The IMD 100 includes one or more processors, such as a programmable microcontroller 220 that controls various operations of the IMD 100, including cardiac monitoring and stimulation therapy. The microcontroller 220 includes a microprocessor (or equivalent control circuitry), one or more processors, RAM and/or ROM memory, logic and timing circuitry, state machine circuitry, and I/O circuitry. The IMD 100 further includes a ventricular pulse generator 222 that generates stimulation pulses for connecting the desired electrodes to the appropriate I/O circuits, thereby facilitating electrode programmability. A switch 226 is controlled by a control signal 228 from the microcontroller 220.

The pulse generator 222 is illustrated in FIG. 2. Optionally, the IMD 100 may include multiple pulse generators, similar to the pulse generator 222, where each pulse generator is coupled to one or more electrodes and controlled by the microcontroller 220 to deliver select stimulus pulse(s) to the corresponding one or more electrodes. The IMD 100 includes sensing circuit 244 selectively coupled to one or more electrodes that perform sensing operations, through the switch 226 to detect the presence of cardiac activity. The output of the sensing circuit 244 is connected to the microcontroller 220 which, in turn, triggers, or inhibits the pulse generator 222 in response to the absence or presence of cardiac activity. The sensing circuit 244 receives a control signal 246 from the microcontroller 220 for purposes of controlling the gain, threshold, polarization charge removal circuitry (not shown), and the timing of any blocking circuitry (not shown) coupled to the inputs of the sensing circuit 244.

In the example of FIG. 2, the sensing circuit 244 is illustrated. Optionally, the IMD 100 may include multiple sensing circuits 244, where each sensing circuit is coupled to one or more electrodes and controlled by the microcontroller 220 to sense electrical activity detected at the corresponding one or more electrodes. The sensing circuit 244 may operate in a unipolar sensing configuration or a bipolar sensing configuration.

The IMD 100 may further include an analog-to-digital (A/D) data acquisition system (DAS) 250 (such as may be or otherwise include an A/D converter) coupled to one or more electrodes via the switch 226 to sample cardiac signals across any pair of desired electrodes. The A/D data acquisition system 250 is configured to acquire intracardiac electrogram signals, convert the raw analog data into digital data and store the digital data for later processing and/or telemetric transmission to an external device 267 (e.g., a programmer, local transceiver, or a diagnostic system analyzer). The A/D acquisition system 250 is controlled by a control signal 256 from the microcontroller 220.

The switch 226 may be coupled to various combinations of one or more leads having one or more electrodes.

The microcontroller 220 is operably coupled to a memory 260 by a suitable data/address bus 262. The programmable operating parameters used by the microcontroller 220 are stored in the memory 260 and used to customize the operation of the IMD 100 to suit the needs of a particular patient. The operating parameters of the IMD 100 may be non-invasively programmed into the memory 260 through a telemetry circuit 264 in telemetric communication via communication link 266 (e.g., MICS, Bluetooth low energy, and/or the like) with the external device 267.

The IMD 100 can further include one or more physiological sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. While shown as being included within the IMD 100, the physiological sensor(s) 270 may be external to the IMD 100, yet still, be implanted within or carried by the patient. Examples of physiological sensors might include sensors that, for example, sense respiration rate, pH of blood, ventricular gradient, activity, position/posture, minute ventilation, and/or the like.

A battery 272 provides operating power to all of the components in the IMD 100. The battery 272 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the IMD 100 employs lithium/silver vanadium oxide batteries.

The IMD 100 further includes an impedance measuring circuit 274, which can be used for many things, including sensing respiration phase. The impedance measuring circuit 274 is coupled to the switch 226 so that any desired electrode and/or terminal may be used to measure impedance in connection with monitoring respiration phase. The IMD 100 is further equipped with a communication modem (modulator/demodulator) 240 to enable wireless communication with other devices, implanted devices and/or external devices. In one implementation, the communication modem 240 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The microcontroller 220 further controls a shocking circuit 280 by way of a timing control 232. The shocking circuit 280 generates shocking pulses, such as MV shocks, LV shocks, etc., as controlled by the microcontroller 220. In accordance with some embodiments, the shocking circuit 280 includes a single change storage capacitor that delivers entire phase I and phase II therapies. The shocking circuit 280 is controlled by the microcontroller 220 by a control signal 282. Optionally, the microcontroller 220 may generate the control signals to shape MV and LV shocks.

Although not shown, the microcontroller 220 may further include other dedicated circuitry and/or firmware/software components that assist in monitoring various conditions of the patient's heart and managing pacing therapies. The microcontroller 220 further an arrhythmia detector 234, a morphology detector 236 and a multi-phase VF therapy controller 233. The timing control 232 is used to control various timing parameters, such as stimulation pulses (e.g., pacing rate, atria-ventricular (AV) delay, atrial interconduction (A-A) delay, ventricular interconduction (V-V) delay, etc.) as well as to keep track of the timing of RR-intervals, refractory periods, blanking intervals, noise detection windows, evoked response windows, alert intervals, marker channel timing, and the like. The timing control 232 controls a timing for delivering the phase I, II and III therapies in a coordinated manner. The timing control 232 controls the phase II and III therapy timed relative to the MV shocks to cooperate with the MV shocks to terminate fibrillation waves of the ventricular arrhythmia episode and to reduce a defibrillation threshold of the heart below a shock-only defibrillation threshold.

The morphology detector 236 is configured to review and analyze one or more features of the morphology of CA signals. For example, in accordance with embodiments herein, the morphology detector 236 may analyze the morphology of detected R waves, where such morphology is then utilized to determine whether to include or exclude one or more beats from further analysis. For example, the morphology detector 236 may be utilized to identify non-conducted ventricular events, such as ventricular fibrillation and the like.

The arrhythmia detector 234 is configured to apply one or more arrhythmia detection algorithms for detecting arrhythmia conditions. By way of example, the arrhythmia detector 234 may apply various VF detection algorithms. The arrhythmia detector 234 is configured to declare a ventricular fibrillation (VF) episode based on the cardiac events.

The therapy controller 233 is configured to perform the operations described herein. The therapy controller 233 is configured to identify a multi-phase VF therapy based on the ventricular fibrillation episode, the multi-phase VF therapy including MV shocks, LV shocks and a pacing therapy. The therapy controller 233 is configured to manage delivery of the burst pacing therapy at a pacing site in a coordinated manner after the MV and LV shocks. The pacing site is located at one of a left ventricular (LV) site or a right ventricular (RV) site. The therapy controller 233 is configured to manage delivery of the MV shock along a shocking vector between shocking electrodes.

The therapy controller 233 is further configured to analyze a timing of VF beats to obtain at least one of a VF cycle length (CL) or variation and to determine at least one of a number of pulses in a pulse train of the burst pacing therapy or a duration of pulse train of the burst pacing therapy based on at least one of the VF cycle length or variation. The therapy controller 233 may be further configured to set a timing delay to time the burst pacing therapy such that one or more of pulses therefrom occur during a period of time in which a local tissue region surrounding the pacing site is excitable and not refractory. The therapy controller 233 may be configured to set a frequency of the burst pacing therapy at a high frequency relative to a cycle length of non-fibrillation arrhythmias.

In accordance with embodiments, the IMD 100 may represent a subcutaneous implantable cardioverter defibrillator (S-ICD). Optionally, the communication modem 240 may be configured to wirelessly communicate with a leadless pacemaker, such as to pass timing information there between. The S-ICD may deliver all or part of the therapy. Additionally or alternatively, the leadless pacemaker may deliver all or part of the therapy.

Figure 3:
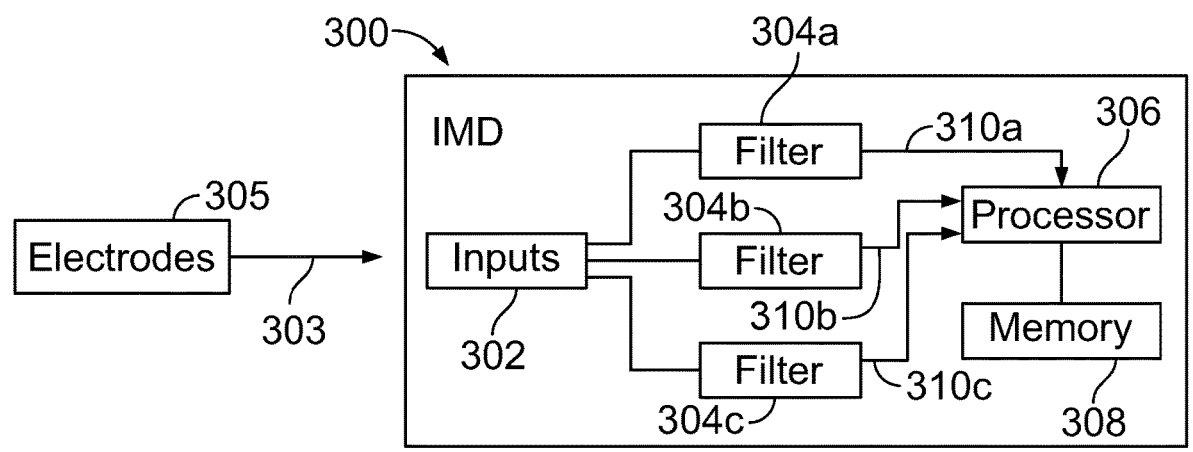
FIG. 3 illustrates a block diagram of an exemplary IMD in accordance with embodiments herein.

FIG. 3 illustrates a block diagram of an exemplary IMD 300 in accordance with embodiments herein. The SIMD 14 shown in FIGS. 1A and 1B, and the IMD 100 shown in FIG. 2 can be configured (or further configured) as shown and described with respect to FIG. 3.

The IMD 300 includes one or more inputs 302, such as which are configured to receive one or more sensed signals 303 from one or more electrodes 305, such as the electrodes 22 and 24 shown in FIGS. 1A and 1B. In at least one embodiment, the one or more sensed signals 303 are sensed electrogram (EGM) signals. In at least one embodiment, the one or more sensed signals 303 are sensed electrocardiogram (ECG) signals.

The IMD 300 also includes a plurality of filters 304a, 304b, and 304c. As shown in FIG. 3, the IMD 300 can includes three filters 304a, 304b, and 304c. Optionally, the IMD 300 can include more than three filters. For example, the IMD 300 can include four or more filters. As another option, the IMD 300 can include less than three filters. For example, the IMD 300 can include two filters. Each of the filters 304a, 304b, and 304c can be configured as a low pass filter, a high pass filter, a band pass filter, a band stop filter, and/or the like.

The filters 304a, 304b, and 304c are in communication with one or more processors 306, such as through one or more wired or wireless connections. For example, the microcontroller 220 shown in FIG. 2 is an example of the processor(s) 306. The processor 306 is also in communication with a memory 308, such as through one or more wired or wireless connections. For example, the memory 260 shown in FIG. 2 is an example of the memory 308. The memory 308 is configured to store one or more sets of filter parameters for the filters 304a, 304b, and 304c.

As shown, the IMD 300 includes the processor(s) 306. Optionally, the processor(s) 306 can be remote from the IMD 300 and in communication with the IMD 300 through one or more communication devices. For example, the external device 267 shown in FIG. 2 can include the one or more processor(s) 306.

The inputs 302 of the IMD 300 are configured to receive the sensed signal(s) 303 from one or more of the electrodes 305. The sensed signal(s) 303 include frequency components associated with physiological activity. The sensed signal(s) 303 can also include frequency components associated with noise.

The filters 304a, 304b, and 304c are in communication with the inputs 302, such as through one or more wired or wireless connections. The filters 304a, 304b, and 304c receive the sensed signal(s) 303 from the inputs 302. Each filter 304a, 304b, and 304c filters the sensed signal(s) 303, and outputs a separate filtered signal representative of a filtered version of the sensed signal(s) 303. For example, the filter 304a outputs a filtered signal 310a; the filter 304b outputs a filtered signal 310b; and the filter 304c outputs a filtered signal 310c.

The processor 306 receives the filtered signals 310a, 310b, and 310c from the filters 304a, 304b, and 304c, respectively. The processor 306 optimizes filter settings (for example, selects a desired one of the filters, and/or varies one of more filter settings thereof) for the IMD 300 based on analysis of the filtered signals 310a, 310b, and 310c. In at least one embodiment, the sensed signals 303 are collected from an individual during sinus rhythm (SR), ventricular tachycardia (VT), and/or ventricular fibrillation (VF).

The memory 308 stores program instructions. The program instructions include data for determining and implementing optimal filter settings that result in accurate (for example, the most accurate) R-wave sensing. In at least one embodiment, the program instructions also include data for periodically reevaluating and updating filter settings if necessary, in order to adapt to changing EGM morphology due to cardiac remodeling and disease progression. The processor 306 executes the program instructions.

As an example, during an implantation process of the IMD 300 into an individual, the electrodes 305 provide the sensed signals 303. The sensed signals 303 can include one or more of an SR, VT, and/or VF, such as may be currently detected, or recorded from a previous test.

The filters 304a, 304b, and 304c filter the sensed signals 303 (such as the SR, VT, and VF signals). In at least one embodiment, the filters 304a, 304b, and 304c are narrowband filters. For example, the filter 304a can be a 6-30 Hz narrowband filter; the filter 304b can be an 8-30 Hz narrowband filter, the filter 304c can be a 10-30 Hz narrowband filter; and another filter (not shown) can be a 12-30 Hz narrowband filter. The upper limit of 30 Hz for the filters 304a-c can be based on R-wave sensing. For example, a majority of R-wave signals are within 5-30 Hz. The upper limit of 30 Hz for the filters 304a, 304b, and 304c can be set to bracket around R-wave signals. Increasing the upper limit beyond 30 Hz can lead to increased noise in the filtered signals 310a, 310b, and 310c. Optionally, the upper limit can be greater than 30 Hz, and the lower limit can be less than 5 Hz.

The processor 306 analyzes the filtered signals 310a, 310b, and 310c and automatically determines an optimal filter setting. For example, in response to analyzing the plurality of filtered signals 310a, 310b, and 310c, the processor 306 selects which of the filters 304a, 304b, or 304c to filter the sensed signals 303 moving forward. In at least one embodiment, the processor 306 selects an optimal filter (one or the filters 304a, 304b, or 304c) based on or more criteria that differentiates among the plurality of filter signals 310a, 310b, and 310c, such as may be determined via scoring. For example, the processor 306 is configured to select an optimal or preferred filter 304a, 304b, or 304c based on a determination of which has the highest score as calculated using raw signals (for example, a sensed signal 303) and filtered signals 310a, 310b, and 310c, such as may be raw and filtered EGM signals during SR and VT/VF. In response to determining the optimal filter for use, the processor 306 then programs the IMD 300 to use the optimal filter (for example, one of the filters 304a, 304b, or 304c), while refraining from the using the other filters (for example, the remainder of the filters 304a, 304b, or 304c).

After the optimal filter has been selected and programmed for use in the IMD 300, the processor 306 periodically receives the filtered signals from all of the filters 304a, 304b, and 304c to determine whether the optimal filter is to be changed. The periodic analysis all of the filtered signals 310a, 310b, and 310c can be a predetermined time period, such as once every week, month, or year), which can be stored in the program instructions in the memory 308. As another example, the periodic analysis can be triggered by one or more specific conditions, such as a daily R-wave amplitude below a predetermined threshold, which can be stored in the program instructions in the memory 308.

In at least one embodiment, the optimal filter can also be selected by an individual, such as a physician. For example, the individual can determine the optimal filter via communication with the IMD 300, such as via a communication device, a could portal, and/or the like. The individual can have access to advance signal analytics (for example, R-wave amplitude history, EGM power spectral density, and/or the like), and filter parameters (for example, filter type, cutoff frequencies, filter order, and/or the like).

As described herein, a system 301 includes the IMD 300, which, includes one or more inputs 302 configured to receive one or more sensed signals 303 from one or more electrodes 305. The IMD 300 further includes a plurality of filters 304a-c configured to filter the one or more sensed signals 303 and output a plurality of filtered signals 310a-c, respectively. The memory 3-8 is configured to store program instructions. The processor 306, when executing the program instructions, is configured to receive the plurality of filtered signals 310a-c, and analyze the plurality of filtered signals 310a-c to determine a desired one of the plurality of filters. In at least one embodiment, the one or more sensed signals 303 are received by the one or more inputs 302 when the IMD 300 is implanted into an individual.

In at least one embodiment, the processor 306 is configured to determine the desired one of the plurality of filters 304a, 304b, or 304c based on one or more criteria that differentiates among the plurality of filter signals. For example, the one or more criteria are determined by the processor 306 via scoring.

In at least one embodiment, the processor 306 is further configured to program the IMD 300 to use the desired one of the plurality of filters 304a, 304b, or 304c and refrain from using the other (such as the other two) of the plurality of filters 304a, 304b, or 304c.

In at least one embodiment, the processor 306 is further configured to periodically analyze the plurality of filtered signals 310a-c based on one or more triggering events. For example, the one or more triggering events include a predetermined time period and/or an R-wave amplitude below a predetermined threshold.

Figure 4:
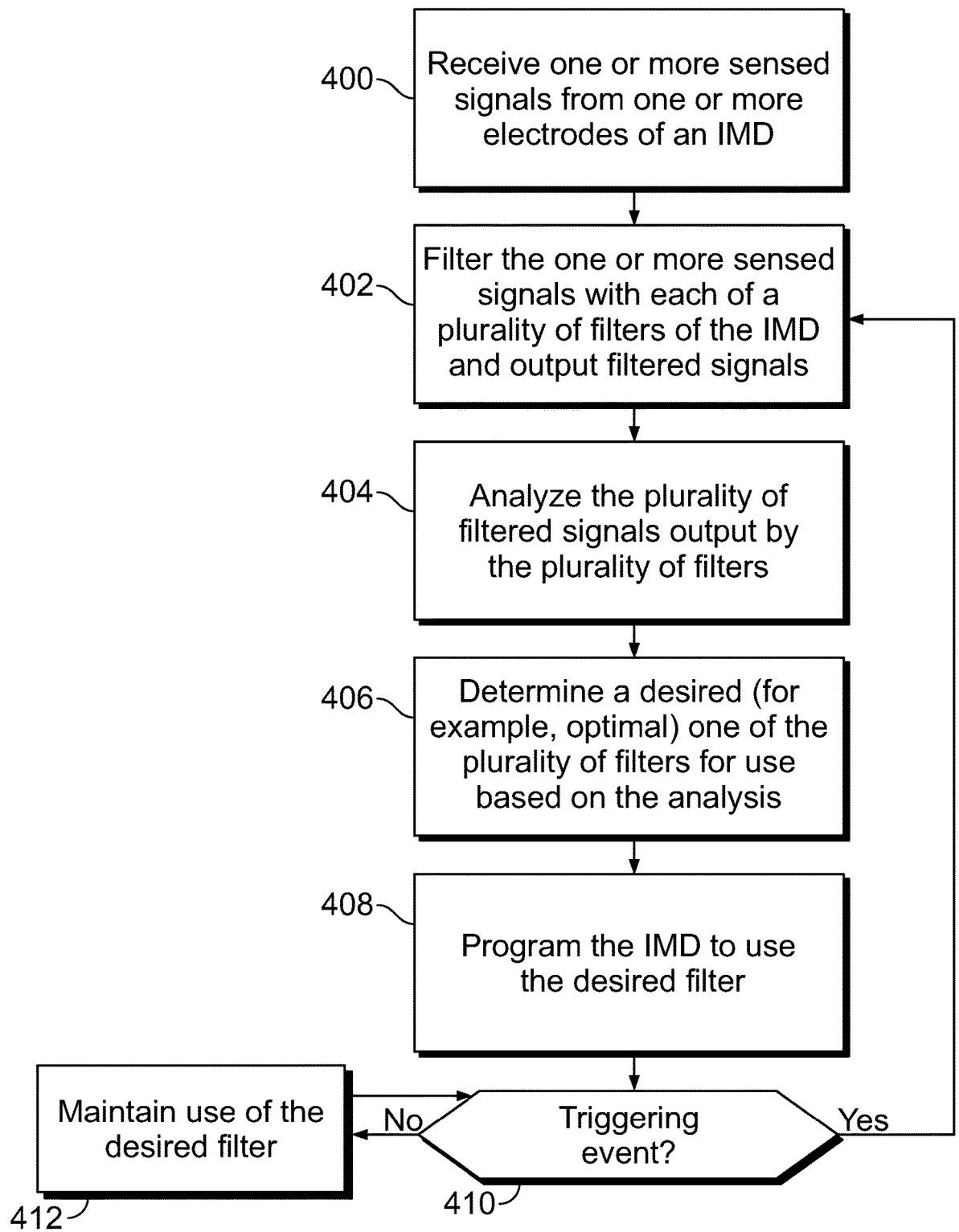
FIG. 4 illustrates a flow chart of a method in accordance with embodiments herein.

FIG. 4 illustrates a flow chart of a method in accordance with embodiments herein. Referring to FIGS. 3 and 4, the method begins at 400, at which the processor 306 receives one or more sensed signals 303 from one or more electrodes 305 of the IMD 300, such as when the IMD 300 is implanted into an individual.

At 402, the one or more sensed signals 303 are filtered by each of a plurality of filters of the IMD 300 (such as the filters 304a, 304b, and 304c). The filters output filtered signals (such as the filtered signals 310a, 310b, and 310c), which are representative of the sensed signal(s) 303, after being filtered.

At 404, one or more processors, such as the processor 306, analyzes the plurality of filtered signals. At 406, the one or more processors determine a desired (for example, optimal or select) one of the plurality of filters for used based on the analyzing step 402. At 408, the one or more processors then program the IMD 300 to use the desired one of the filters.

At 410, the one or more processors determine if a triggering event has occurred. The triggering event can be a predetermined periodic time period (such as after a month, multiple months, a year, or the like), or a specific condition of the individual having the IMD 300 (such as a daily average R-wave amplitude below a predetermined threshold). If no triggering event has occurred at 410, the method proceeds to 412, at which the use of the desired one of the filters is maintained. The method may then return to 410. If, however, a triggering event has occurred at 410, the method returns to 402.

In at least one embodiment, the plurality of filters (such as the filters 304a, 304b, and 304c) can have fixed filter settings. Optionally, the one or more processors can change one or more of filter settings (such as via firmware) to achieve a more desirable (for example, optimal) filter. As an example, the one or more processors can receive adapted or otherwise different filter settings from the external device 267 and update a particular filter 304a-c based on the received different filter settings. In this manner, the one or more processors can adapt each of the filters 304a-c to different filter settings.

In at least one embodiment, the one or more processors can select a desired (for example, optimal) filter from the plurality of filters 304a-c as the received signal 303 changes over time. For example, the received signal 303 can change based on physical shifting of the IMD 300 in relation to the individual having the IMD 300, physiological changes of the individual, different posture of the individual (for example, standing, sitting, or laying down), and other aspects that can affect morphology of the sensed signals 303. The one or more processors can continually monitor the received signal 303 and filtered signals 310a-c over time and selectively determine the desired filter 304a, 304b, or 304c for use based on changing circumstances.

As described herein, embodiments provide systems and methods for personalizing filter settings (for example, selecting a desired one of a plurality of filters). In at least one embodiment, one or more processors (such as the processor 306) determines (and optionally periodically determines, based a triggering event) a desired (for example, optimal) filter for use. For example, the desired filter can be selected based on an individual's most recent EGM morphology. As a further example, the one or more processors automatically reprogram the IMD 300 to use the desired filter. As a further example, the one or more processors periodically collect and store the one or more sensed signals 303 (for example, EGM during SR and VT/VF) for future filter optimization.

In at least one embodiment, the system and method to select a desired filter can be activated during an implantation procedure. The one or more processors evaluate a collection of pre-designed filters (for example, the filters 304a-c) in relation to SR EGM obtained during the implantation procedure. EGM recorded during VT/VF can also be used to evaluate the filters 304a-c, such as if defibrillation threshold (DFT) testing was performed during the implantation procedure. Each of the collection of filters 304a-c can have different filter parameters that include but are not limited to cut-off frequencies, filter type, filter order, and/or the like.

The one or more processors automatically determine the desired filter for the individual based on one or more criteria. Alternatively, a user can also manually select, visualize, and program various digital filter parameters on a user-interface client such as a programmer or a cloud portal. The user-interface client may also provide advanced signal analytics such as R-wave amplitude trend, EGM power spectral density to help guide the decision-making when optimizing filter parameters. The client may also provide greater and finer control of the filter parameters for users to fine-tune the desired filter for the individual. The programmable parameters may include order of digital filter (for steeper roll-off in the transition band), filter corner frequencies, type of digital filter (for example, Butterworth, Chebyshev, Elliptic, and/or the like), and gain of filtered signals.

After the one or more processors determine the desired filter, the one or more processors program the IMD 300 to use the desired filter, such as to filter signals for R-wave sensing. In at least one embodiment, during operation, the one or more processors periodically collect and store sensed signals 303, such as EGM (for example, a single beat, a series of beats, or an ensemble average of a series of beats) during SR and VT/VF, which are used to evaluate filter settings either periodically or when triggered by specific conditions, such as when R-wave amplitude during SR or VT/VF is below a threshold. The entire process can be repeated to determine the optimal filter setting (that is, the optimal or otherwise desired filter among the plurality of filters) based on a most recent EGM morphology. When running continuously, the one or more processors ensure that the filter settings adapt to the changing frequency content and morphology of an individual's EGM caused by cardiac remodeling and disease progression.

Figure 5:
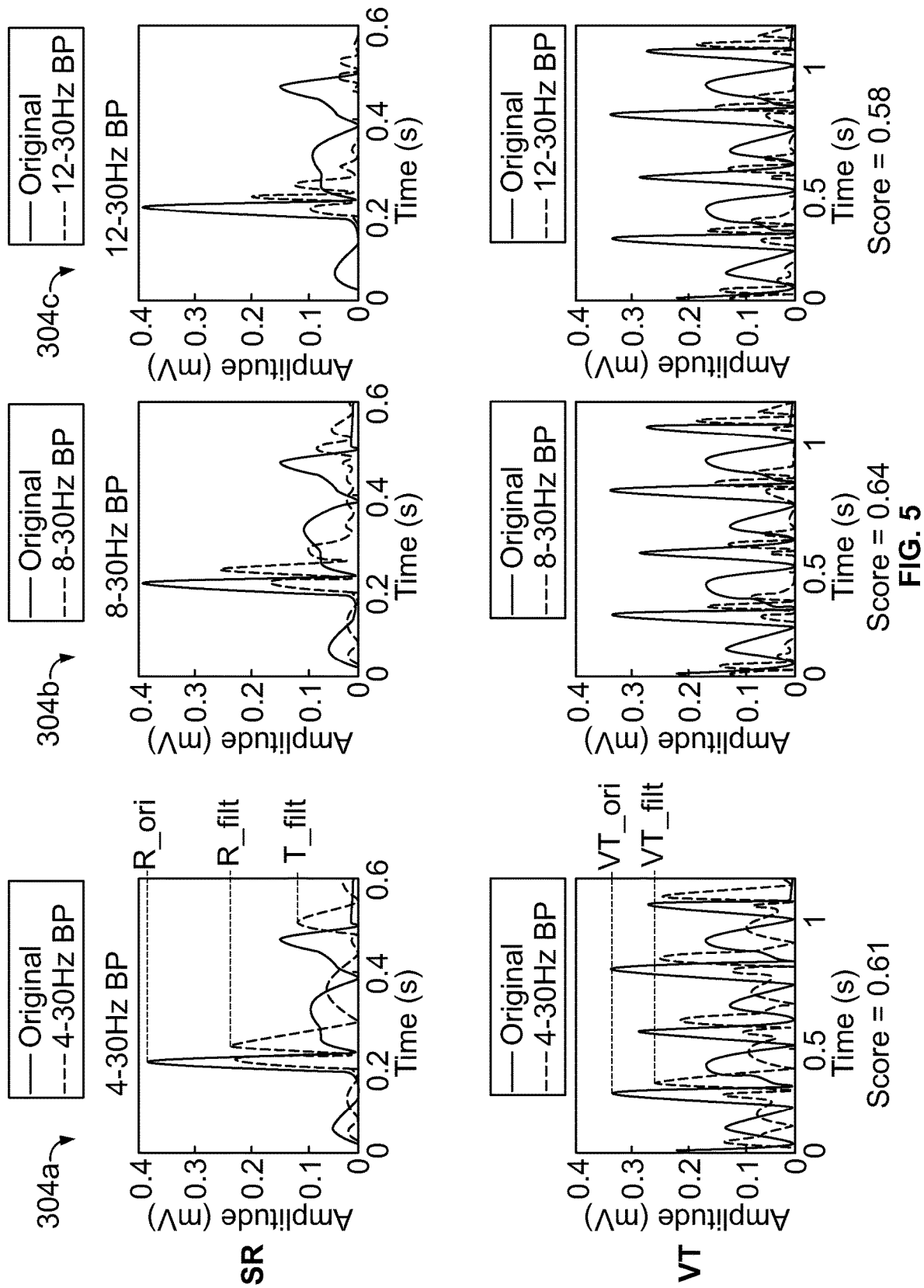
FIG. 5 illustrates charts regarding filter score determination for a plurality of filters in accordance with embodiments herein.

FIG. 5 illustrates charts regarding filter score determination for a plurality of filters 304a, 304b, and 304c in accordance with embodiments herein. For example, the filter 304a can be a 4-30 Hz band pass filter; the filter 304b can be a 8-30 Hz bandpass filter; and the filter 304c can be a 12-30 Hz bandpass filter. Referring to FIGS. 3-5, the one or more processors (such as the processor 306) analyzes the filtered signals 310a, 310b, and 310c output by the filters 304a, 304b, and 304c, respectively, by determining respective filter scores. The line in each chart referring to "original" is for the original, unfiltered sensed signal 303. The lines referring to "4-30 Hz BP," "8-30 Hz BP," and "12-30 Hz BP" in the charts refer to the respective filtered signals 310a, 310b, and 310c.

As noted, the one or more processors are configured to automatically determine the desired filter for the individual having the IMD 300 based on one or more criteria, an example of which is illustrated in FIG. 5. As shown in FIG. 5, a segment of EGM during SR and VT are filtered by the three filters 304a, 304b, and 304c, which can be second-order Butterworth band-pass filters with different corner frequencies, which include 4-30 Hz, 8-30 Hz, and 12-30 Hz. Characteristics of the original and filtered EGM during SR and VT were used to determine the desired filter for the individual having the IMD 300.

In particular, an original (that is, sensed, but unfiltered) R-wave amplitude ($R_{ori}$), filtered R-wave amplitude ($R_{filt}$), filtered T-wave amplitude ($T_{filt}$), original R-wave amplitude during VT ($VT_{ori}$), and filtered R-wave amplitude during VT ($VT_{filt}$) are used to calculate the filter score to quantify the performance of each filter 304a, 304b, and 30c using the equation below:

$$\text{score} = w1 \times \frac{R_{filt}}{R_{ori}} + w2 \times \frac{VT_{filt}}{VT_{ori}} + w3 \times \left(1 - \frac{T_{filt}}{R_{filt}}\right)$$

where w1, w2, and w3 are weights that specify the contribution of each ratio to the score. For example, the nominal values for w1, w2, and w3 are 0.2, 0.3, and 0.5, respectively. As shown above, the score is calculated based on three ratios that quantify 1) the attenuation of R-wave during SR, 2) the attenuation of R-wave during VT, and 3) the attenuation of T waves by a filter. Because the weights (w1, w2, and w3) add up to 1, an ideal filter that does not attenuate R-waves during SR and VT and completely attenuate T-waves would achieve a score of 1. In addition, values of w1, w2, and w3 may be adjusted based on an individual's medical history (primary vs. secondary prevention, history of conduction abnormalities, hypertrophies, and ischemia).

As shown in FIG. 5, the filter 304b (such as a bandpass filter with 8-30 Hz corner frequencies) significantly attenuates the T-waves while largely preserving the R-wave amplitude during SR and VT, thereby achieving the highest score among the three filters 304a, 304b, and 304c in the comparison.

Figure 6:
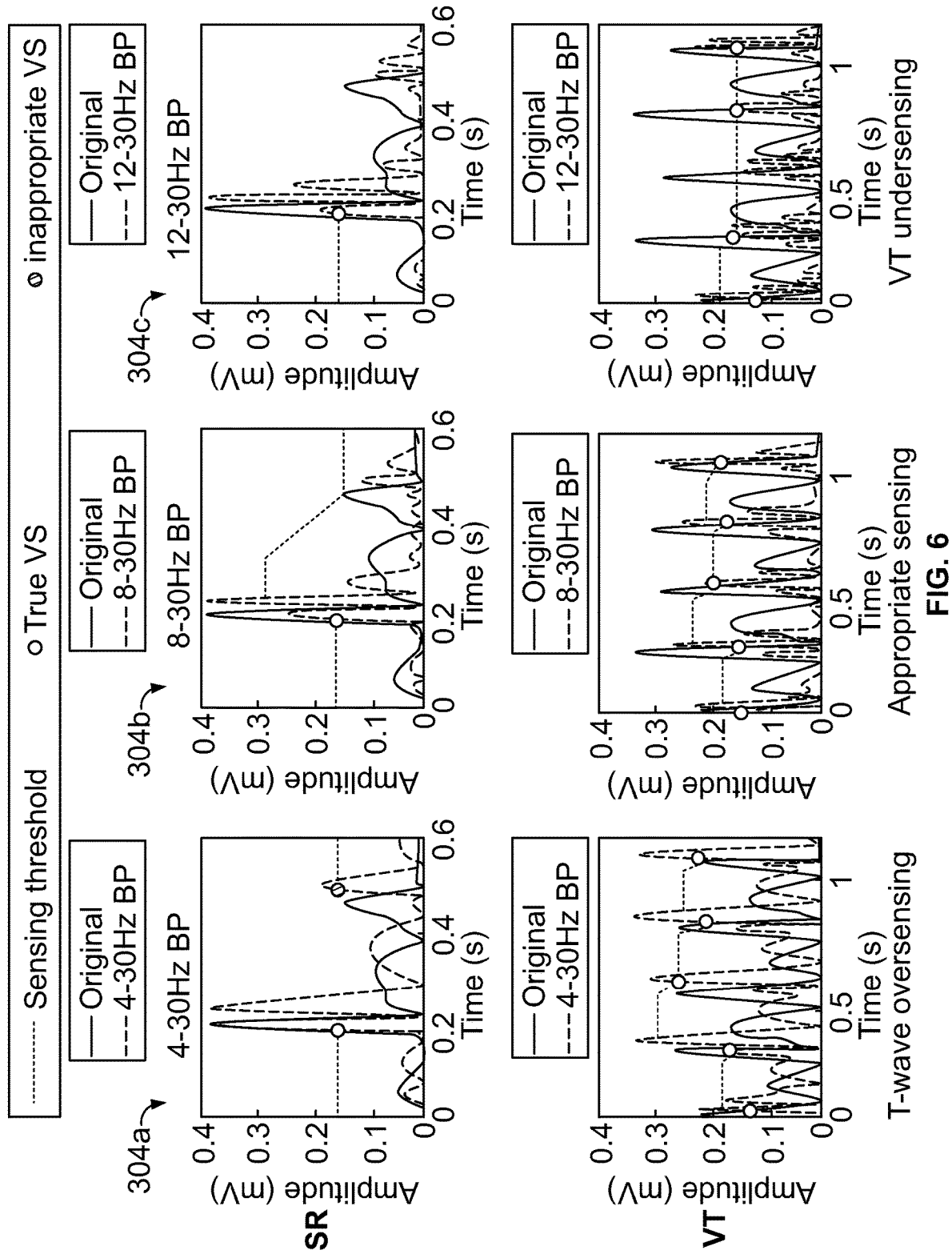
FIG. 6 illustrates charts regarding a desired filter (such as exhibiting the highest filter score) resulting in appropriate ventricular sensed (VS) detection (compared to non-selected filters 304a and 304c) in accordance with embodiments herein.

FIG. 6 illustrates charts regarding a desired filter 304b (such as exhibiting the highest filter score) resulting in appropriate ventricular sensed (VS) detection (compared to non-selected filters 304a and 304c) in accordance with embodiments herein. As shown in FIG. 6, the filtered signals are scaled to match an amplitude of the original signal. At a max sensitivity of 0.15 mV, the filters 304a and 304c with lower scores resulted in either T-wave oversensing due to insufficient T-wave attenuation or R-wave undersensing during VT due to over-attenuation of VT morphology.

In at least one embodiment, a system can be used to train and/or calibrate one or more filters (such as filters 304a-c), such as described in U.S. Pat. No. 9,427,594, entitled "Method and System for Tracking Events of Interest Between Leadless and Subcutaneous Implantable Cardioverter Devices," which is incorporated by reference in its entirety.

In at least one embodiment, posture and/or activity can be utilized by the system to modify and or select properties of the filters 304a-c, for example. For example, one of the filters 304a-c can be selected that is optimized for use across all postures, and/or the device can be trained (such as during implantation), such as via an accelerometer, to select filter parameters that detect R-waves at different postures. Surface EKGs can be used for feedback and comparison. The filter set can further be modified with changing posture automatically or in the event of detection (for example, VT, VF, or the like) the device could detect posture and modify filter setting and then confirm or reject event detection using modified parameters.

As described herein, embodiments provide systems and methods for optimizing filter settings of an IMD of an individual based on individual-specific electrocardiogram signals, thereby increasing the ability of the IMD to attenuate unwanted signals (for example, P and T waves) while preserving R-wave amplitude. Accordingly, embodiments provide increased accuracy and robustness of R-wave sensing.

Alternative Embodiments Incorporating External Devices

Figure 7:
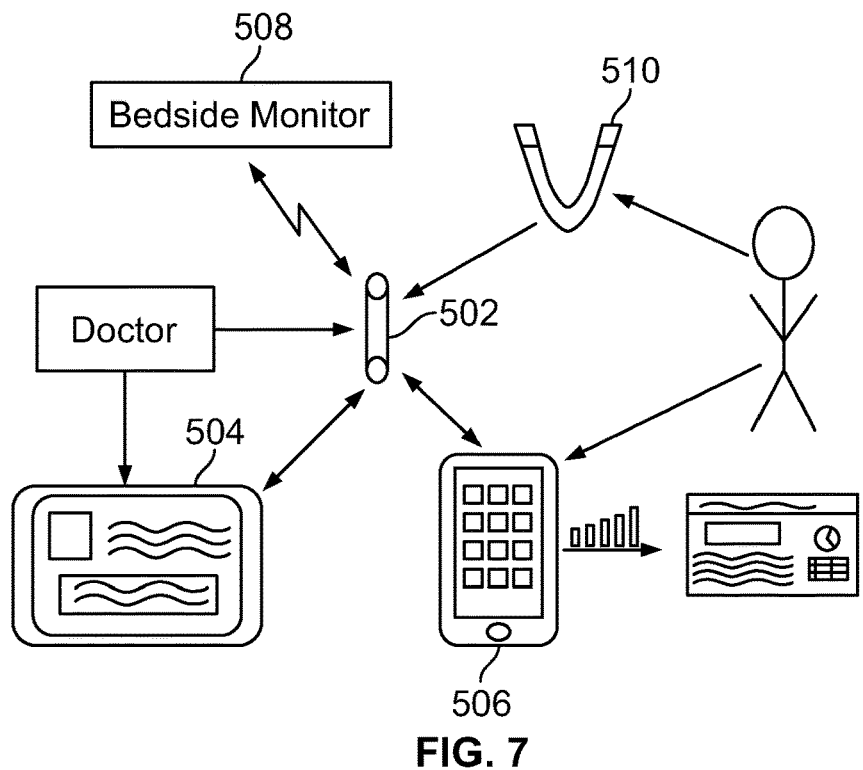
FIG. 7 illustrates a system level diagram indicating potential devices and networks that utilize the methods and systems herein.

FIG. 7 illustrates a system level diagram indicating potential devices and networks that utilize the methods and systems herein. For example, an IMD 502 (e.g., IMD 300 of FIG. 3) may be utilized to collect a cardiac activity (CA) data set that can be interfered with as a result of extrinsic noise in an environment. The IMD 502 may supply a CA data set (CA signals, sensitivity levels, and motion data) to various local EDs, such as a tablet device 504, a smart phone 506, a bedside monitoring device 508, a smart watch and the like. The devices 504-508 include a display to present the various types of the CA signals, markers, statistics, diagnostics, and other information described herein.

The IMD 502 may convey the CA data set over various types of wireless communications links to the devices 504, 506 and 508. The IMD 502 may utilize various communications protocols and be activated in various manners, such as through a Bluetooth, Bluetooth low energy, Wi-Fi, or other wireless protocol. Additionally or alternatively, when a magnetic device 510 is held next to the patient, the magnetic field from the device 510 may activate the IMD 502 to transmit the CA data set to one or more of the devices 504-508.

The processes described herein may be implemented on or utilizing one or more of the devices 504-508. In particular, the devices 504-508 can include a GPS, determine network changes, include scheduling information and timers, etc. that can be utilized to determine the environment of the IMD, and provide FC instructions for an IMD.

Figure 8:
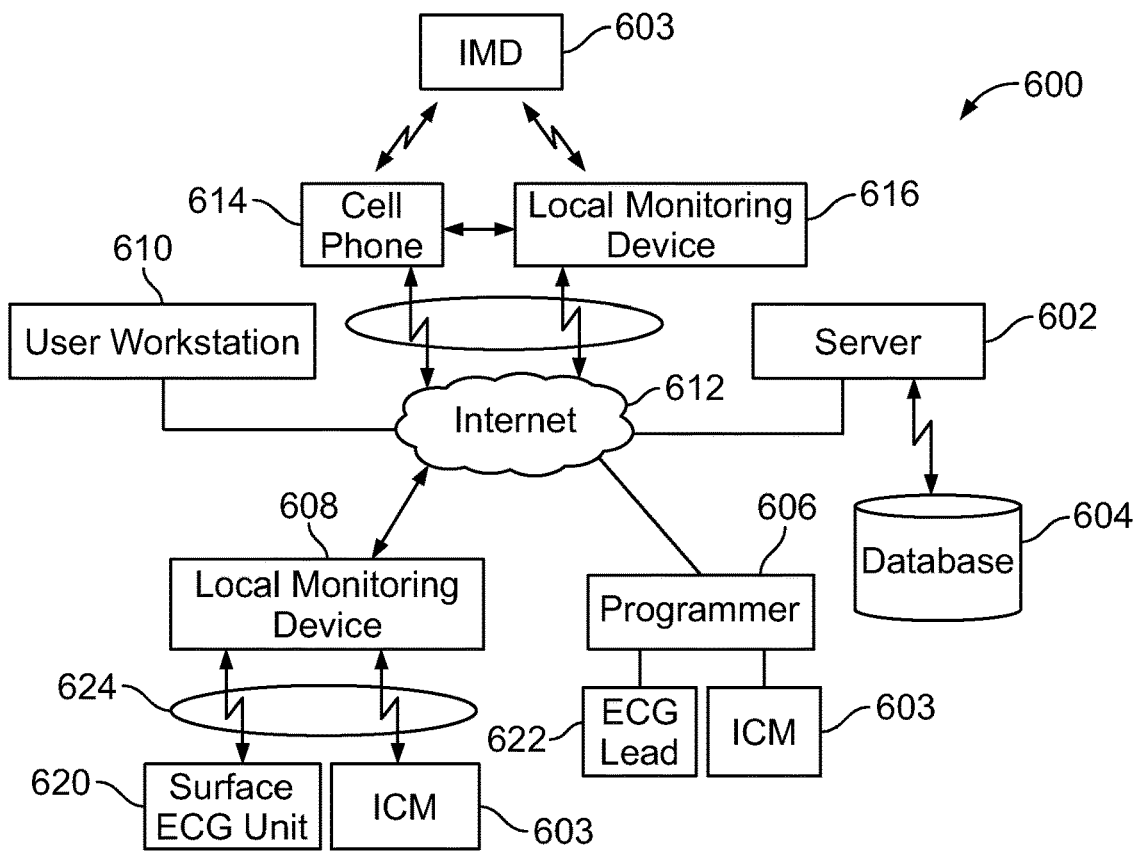
FIG. 8 illustrates a distributed processing system in accordance with embodiments herein.

FIG. 8 illustrates a distributed processing system 600 in accordance with embodiments herein. The distributed processing system 600 includes a server 602 connected to a database 604, a programmer 606, a local monitoring device 608 (for example, IMD 300 shown in FIG. 3) and a user workstation 610 electrically connected to a network 612. Any processor-based components (e.g., workstation 610, cell phone 614, local monitoring device 616, server 602, programmer 606) may perform the processes discussed herein.

The network 612 may provide cloud-based services over the internet, a voice over IP (VoIP) gateway, a local plain old telephone service (POTS), a public switched telephone network (PSTN), a cellular phone-based network, and the like. Alternatively, the communication system may be a local area network (LAN), a medical campus area network (CAN), a metropolitan area network (MAN), or a wide area network (WAM). The communication system serves to provide a network that facilitates the transfer/receipt of data and other information between local and remote devices (relative to a patient). The server 602 is a computer system that provides services to the other computing devices on the network 612. The server 602 controls the communication of information such as CA signals, motion data, bradycardia episode information, asystole episode information, arrhythmia episode information, markers, CA signal waveforms, heart rates, and device settings. The server 602 interfaces with the network 612 to transfer information between the programmer 606, local monitoring devices 608, 616, user workstation 610, cell phone 614 and database 604. The database 604 stores information such as CA data, arrhythmia episode information, arrhythmia statistics, diagnostics, markers, CA signal waveforms, heart rates, device settings, and the like, for a patient population. The information is downloaded into the database 604 via the server 602 or, alternatively, the information is uploaded to the server 602 from the database 604. The programmer 606 may reside in a patient's home, a hospital, or a physician's office. The programmer 606 may wirelessly communicate with the IMD 603 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 606 to the IMD 603. The programmer 606 is able to acquire ECG 622 from surface electrodes on a person (e.g., ECGs), electrograms (e.g., EGM) signals from the IMD 603, and/or CA data, arrhythmia episode information, arrhythmia statistics, diagnostics, markers, CA signal waveforms, atrial heart rates, device settings from the IMD 603. The programmer 606 interfaces with the network 612, either via the internet, to upload the information acquired from the surface ECG unit 620, or the IMD 603 to the server 602.

The local monitoring device 608 interfaces with the communication system to upload to the server 602 one or more of the CA signals, motion data, arrhythmia episode information, arrhythmia statistics, diagnostics, markers, CA signal waveforms, heart rates, sensitivity profile parameter settings and detection thresholds. In one embodiment, the surface ECG unit 620 and the IMD 603 have a bi-directional connection 624 with the local RF monitoring device 608 via a wireless connection. The local monitoring device 608 is able to acquire CA signals from the surface of a person, CA data sets and other information from the IMD 603, and/or CA signal waveforms, heart rates, and device settings from the IMD 603, including after filtering of signals for environmental noise. On the other hand, the local monitoring device 608 may download the data and information discussed herein from the database 604 to the surface ECG unit 620 or the IMD 603.

The user workstation 610 may be utilized by a physician or medical personnel to interface with the network 612 to download CA signals, motion data, and other information discussed herein from the database 604, from the local monitoring devices 608, 616, from the IMD 603 or otherwise. Once downloaded, the user workstation 610 may process the CA signals and motion data in accordance with one or more of the operations described above. The user workstation 610 may upload/push settings (e.g., sensitivity profile parameter settings), IMD instructions, other information, and notifications to the cell phone 614, local monitoring devices 608, 616, programmer 606, server 602 and/or IMD 603.

The processes described herein in connection managing environmental based operations may be performed by one or more of the devices illustrated in FIG. 8, including but not limited to the IMD 603, programmer 606, local monitoring devices 608, 616, user workstation 610, cell phone 614, and server 602. The process described herein may be distributed between the devices of FIG. 8.

IMDs and Processes for Inclusion with Alternative Embodiments

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. The IMD may measure electrical and/or mechanical information. For example, the IMD may include one or more structural and/or functional aspects of the device(s) described in U.S. Pat. No. 9,333,351, entitled "Neurostimulation Method And System To Treat Apnea" issued May 10, 2016 and U.S. Pat. No. 9,044,610, entitled "System And Methods For Providing A Distributed Virtual Stimulation Cathode For Use With An Implantable Neurostimulation System" issued Jun. 2, 2015, which are hereby incorporated by reference. The IMD may monitor transthoracic impedance, such as implemented by the CorVue algorithm offered by St. Jude Medical. Additionally or alternatively, the IMD may include one or more structural and/or functional aspects of the device(s) described in U.S. Pat. No. 9,216,285, entitled "Leadless Implantable Medical Device Having Removable And Fixed Components" issued Dec. 22, 2015 and U.S. Pat. No. 8,831,747, entitled "Leadless Neurostimulation Device And Method Including The Same" issued Sep. 9, 2014, which are hereby incorporated by reference. Additionally or alternatively, the IMD may include one or more structural and/or functional aspects of the device(s) described in U.S. Pat. No. 8,391,980, entitled "Method And System For Identifying A Potential Lead Failure In An Implantable Medical Device" issued Mar. 5, 2013 and U.S. Pat. No. 9,232,485, entitled "System And Method For Selectively Communicating With An Implantable Medical Device" issued Jan. 5, 2016, which are hereby incorporated by reference. Additionally or alternatively, the IMD may be a subcutaneous IMD that includes one or more structural and/or functional aspects of the device(s) described in U.S. application Ser. No. 15/973,195, entitled "Subcutaneous Implantation Medical Device With Multiple Parasternal-Anterior Electrodes" filed May 7, 2018; U.S. application Ser. No. 15/973,219, entitled "Implantable Medical Systems And Methods Including Pulse Generators And Leads" filed May 7, 2018; U.S. application Ser. No. 15/973,249, entitled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein. Embodiments may be implemented in connection with one or more subcutaneous implantable medical devices (S-IMDs). For example, the S-IMD may include one or more structural and/or functional aspects of the device(s) described in U.S. application Ser. No. 15/973,219, entitled "IMPLANTABLE MEDICAL SYSTEMS AND METHODS INCLUDING PULSE GENERATORS AND LEADS", filed May 7, 2018; U.S. application Ser. No. 15/973,195, entitled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties. The IMD may represent a passive device that utilizes an external power source, and entirely mechanical plan will device, and/or an active device that includes an internal power source. The IMD may deliver some type of therapy/treatment, provide mechanical circulatory support and/or merely monitor one or more physiologic characteristics of interest (e.g., PAP, CA signals, impedance, heart sounds).

Embodiments herein may be incorporated with the structure and functionality (e.g. detection and analysis of the corresponding types of biological signals and determinations of the corresponding types of non-physiologic conditions) described in any or all of the publications referenced herein, including the following: U.S. patent application Ser. No. 16/930,791, filed Jul. 16, 2020, and titled "METHODS, DEVICES AND SYSTEMS FOR HOLISTIC INTEGRATED HEALTHCARE PATIENT MANAGEMENT"; U.S. Patent Publication Number 2014/0275827, entitled "METHOD AND SYSTEM FOR DERIVING EFFECTIVENESS OF MEDICAL TREATMENT OF A PATIENT" published Sep. 18, 2014; U.S. Patent Publication Number 2014/0039238, entitled "SYSTEMS AND METHODS FOR CONTROLLING NEUROSTIMULATION OF ACUPUNCTURE SITES USING AN IMPLANTABLE CARDIAC RHYTHM MANAGEMENT DEVICE" published Feb. 6, 2014; U.S. Patent Publication Number 2013/0204147, entitled "ATRIAL FIBRILLATION DETECTION BASED ON PULMONARY ARTERY PRESSURE DATA" published Aug. 8, 2013; U.S. Patent Publication Number 2013/0116583, entitled "SYSTEMS AND METHODS FOR PREDICTING AND CORROBORATING PULMONARY FLUID OVERLOADS USING AN IMPLANTABLE MEDICAL DEVICE" published May 9, 2013; U.S. Patent Publication Number 2012/0089032, entitled "METHOD AND SYSTEM FOR DISCRIMINATING AND MONITORING ATRIAL ARRHYTHMIA BASED ON CARDIOGENIC IMPEDANCE" published Apr. 12, 2012; U.S. patent application Ser. No. 11/378,604, filed Mar. 16, 2006, of Kroll et al., entitled, "System and Method for Detecting Arterial Blood Pressure based on Aortic Electrical Resistance using an Implantable Medical Device," now U.S. Pat. No. 7,654,964; U.S. Patent Publication Number 2011/0125206, entitled "SINGLE CHAMBER IMPLANTABLE MEDICAL DEVICE FOR CONFIRMING ARRHYTHMIA THROUGH RETROSPECTIVE CARDIAC SIGNALS" published May 26, 2011; U.S. Patent Publication Number 2014/0221771, entitled "METHOD AND IMPLANTABLE SYSTEM FOR BLOOD-GLUCOSE CONCENTRATION MONITORING USING PARALLEL METHODOLOGIES" published Aug. 7, 2014; U.S. Patent Publication Number 2014/0058278, entitled "SYSTEMS AND METHODS FOR DETECTING ISCHEMIC EVENTS" published Feb. 27, 2014; U.S. Patent Publication Number 2013/0218036, entitled "METHODS AND SYSTEMS TO CORRELATE ARRHYTHMIC AND ISCHEMIC EVENTS" published Aug. 22, 2013; U.S. Patent Publication Number 2012/0197149, entitled "SYSTEM AND METHOD FOR DISTINGUISHING AMONG CARDIAC ISCHEMIA, HYPOGLYCEMIA AND HYPERGLYCEMIA USING AN IMPLANTABLE MEDICAL DEVICE" published Aug. 2, 2012; U.S. Patent Publication Number 2012/0065527, entitled "METHODS AND SYSTEMS FOR MONITORING ATRIAL STIFFNESS" published Mar. 15, 2012; U.S. Patent Publication Number 2012/0046528, entitled "SYSTEM AND METHOD FOR DETECTING AND TREATING CARDIOVASCULAR DISEASE" published Feb. 23, 2012; U.S. Patent Publication Number 2011/0004111, entitled "ISCHEMIA DETECTION USING INTRA-CARDIAC SIGNALS" published Jan. 6, 2011; U.S. Pat. No. 8,514,086, entitled "DISPLAYS FOR A MEDICAL DEVICE", issued Aug. 20, 2013; U.S. Patent Publication Number 2011/0256024, entitled "MODULAR ANALYTE MONITORING DEVICE", published Oct. 20, 2011; U.S. Patent Publication Number 2010/0198142, entitled "MULTIFUNCTION ANALYTE TEST DEVICE AND METHODS THEREFORE", published Aug. 5, 2010; U.S. Patent Publication Number 2011/0160544, entitled "SYSTEM AND METHOD FOR ANALYSIS OF MEDICAL DATA TO ENCOURAGE HEALTHCARE MANAGEMENT", published Jun. 30, 2011; U.S. Pat. No. 5,063,081, entitled "METHOD OF MANUFACTURING A PLURALITY OF UNIFORM MICROFABRICATED SENSING DEVICES HAVING AN IMMOBILIZED LIGAND RECEPTOR" issued Nov. 5, 1991; U.S. Pat. No. 7,419,821, entitled "APPARATUS AND METHODS FOR ANALYTE MEASUREMENT AND IMMUNOASSAY" issued Sep. 2, 2008; U.S. Patent Publication Number 2004/0018577, entitled "MULTIPLE HYBRID IMMUNOASSAYS" published Jan. 29, 2004; U.S. Pat. No. 7,682,833, entitled "IMMUNOASSAY DEVICE WITH IMPROVED SAMPLE CLOSURE" issued Mar. 23, 2010; U.S. Pat. No. 7,723,099, entitled "IMMUNOASSAY DEVICE WITH IMMUNO-REFERENCE ELECTRODE" issued May 25, 2010; Baj-Rossi et al. "FABRICATION AND PACKAGING OF A FULLY IMPLANTABLE BIOSENSOR ARRAY", (2013) IEEE, pages 166-169. U.S. Pat. No. 6,786,874, entitled "APPA- RATUS AND METHOD FOR THE COLLECTION OF INTERSTITIAL FLUIDS" issued Sep. 7, 2004; and U.S. Pat. No. 9,872,641, entitled "METHODS, DEVICES AND SYSTEMS RELATED TO ANALYTE MONITORING" issued Jan. 23, 2018; U.S. patent application Ser. No. 11/387,579, filed Mar. 23, 2006, of Koh, entitled "System and Method for Calibrating a Blood Oxygen Saturation Sensor for use with an Implantable Medical Device," now U.S. Pat. No. 8,099,146; U.S. patent application Ser. No. 11/267,665, filed Nov. 4, 2005, of Kil et al., entitled "System and Method for Measuring Cardiac Output via Thermal Dilution using an Implantable Medical Device with Thermistor Implanted in Right Ventricle," now abandoned; U.S. Patent Publication No. 2005/0215914, to Bornzin et al., entitled "System and Method for Evaluating Heart Failure Based on Ventricular End-Diastolic Volume using an Implantable Medical Device"; U.S. Pat. No. 5,800,467 to Park et al., entitled "Cardio-Synchronous Impedance Measurement System for an Implantable Stimulation Device;" U.S. patent application Ser. No. 11/100,189, filed Apr. 5, 2005, of Koh, entitled "System and Method for Detection of Respiration Patterns via Integration of Intracardiac Electrogram Signals," now U.S. Pat. No. 7,404,799; and in U.S. patent application Ser. No. 11/623,663, filed Jan. 16, 2007, of Zou et al., entitled "Sensor/Lead Systems for use with Implantable Medical Devices," now U.S. Pat. No. 8,388,670.

All references, including publications, patent applications and patents, cited herein are hereby incorporated by reference to the same extent as if each reference were individually and specifically indicated to be incorporated by reference and were set forth in its entirety herein.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices, and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system comprising:
   an implantable medical device (IMD), comprising:
   one or more inputs configured to receive one or more sensed signals from one or more electrodes;
   a plurality of filters configured to filter the one or more sensed signals and output a plurality of filtered signals such that a first filter of the plurality of filters is configured to filter a first sensed signal of the one or more sensed signals and output a first filtered signal of the plurality of filtered signals, and a second filter of the plurality of filters is configured to filter the first sensed signal and output a second filtered signal of the plurality of filtered signals;
   memory configured to store program instructions; and
   a processor that, when executing the program instructions, is configured to:
   receive the plurality of filtered signals;
   analyze the plurality of filtered signals to determine a desired one of the plurality of filters; and
   in response to the analysis, program the IMD to use the desired one of the plurality of filters and refrain from using the other of the plurality of filters.

2. The system of claim 1, wherein the one or more sensed signals comprise one or more sensed electrogram (EGM) signals.

3. The system of claim 1, wherein each of the plurality of filters is configured as a low pass filter, a high pass filter, a band pass filter, or a band stop filter.

4. The system of claim 1, wherein the one or more sensed signals are collected from an individual during one or more of sinus rhythm (SR), ventricular tachycardia (VT), or ventricular fibrillation (VF).

5. The system of claim 1, wherein the one or more sensed signals are received by the one or more inputs when the IMD is implanted into an individual.

6. The system of claim 1, wherein the plurality of filters comprise:
   a 6-30 Hz bandpass filter;
   an 8-30 Hz bandpass filter;
   a 10-30 Hz bandpass filter; and
   a 12-30 Hz bandpass filter.

7. The system of claim 1, wherein the processor is configured to determine the desired one of the plurality of filters based on one or more criteria that differentiates among the plurality of filtered signals.

8. The system of claim 7, wherein the one or more criteria are determined by the processor via scoring.

9. The system of claim 8, wherein the processor is configured to score the plurality of filtered signals through analysis of an original R-wave amplitude ($R_{ori}$), filtered R-wave amplitude ($R_{filt}$), filtered T-wave amplitude ($T_{filt}$), original R-wave amplitude during VT ($VT_{ori}$) or VF, and filtered R-wave amplitude during VT ($VT_{filt}$) or VF to quantify a performance of each of the plurality of filters in accordance with the following equation:

$$\text{score} = w1 \times \frac{R_{filt}}{R_{ori}} + w2 \times \frac{VT_{filt}}{VT_{ori}} + w3 \times \left(1 - \frac{T_{filt}}{R_{filt}}\right)$$

where w1, w2, and w3 are weights.

10. The system of claim 1, wherein the processor is further configured to periodically analyze the plurality of filtered signals based on one or more triggering events.

11. The system of claim 10, wherein the one or more triggering events comprises one or both of a predetermined time period or an R-wave amplitude below a predetermined threshold.

12. The system of claim 1, wherein the processor is configured to determine the desired one of the plurality of filters via scoring the plurality of filter signals based on at least: (i) attenuation of R-waves during sinus rhythm (SR) and (ii) attenuation of R-waves during ventricular tachycardia (VT) or ventricular fibrillation (VF).

13. A computer implemented method, under control of one or more processors, where the one or more processors are configured with specific executable instructions, the computer implemented method comprising:
   receiving, by one or more inputs, one or more sensed signals from one or more electrodes;
   filtering, by a plurality of filters, the one or more sensed signals such that a first filter of the plurality of filters filters a first sensed signal of the one or more sensed signals and outputs a first filtered signal of the plurality of filtered signals, and a second filter of the plurality of filters filters the first sensed signal and outputs a second filtered signal of the plurality of filtered signals;

receiving the plurality of filtered signals from the plurality of filters;
analyzing the plurality of filtered signals;
determining, via said analyzing, a desired one of the plurality of filters; and
programming the IMD to use the desired one of the plurality of filters and refrain from using the other of the plurality of filters.

14. The computer implemented method of claim 13, wherein the one or more sensed signals comprise one or more sensed electrogram (EGM) signals.

15. The computer implemented method of claim 13, wherein each of the plurality of filters is configured as a low pass filter, a high pass filter, a band pass filter, or a band stop filter.

16. The computer implemented method of claim 13, wherein the one or more sensed signals are collected from an individual during one or more of sinus rhythm (SR), ventricular tachycardia (VT), or ventricular fibrillation (VF).

17. The computer implemented method of claim 13, wherein the one or more sensed signals are received by the one or more inputs when the IMD is implanted into an individual.

18. The computer implemented method of claim 13, wherein said determining is based on one or more criteria that differentiates among the plurality of filtered signals.

19. The computer implemented method of claim 13, said analyzing comprises scoring the plurality of filtered signals through analysis of an original R-wave amplitude ($R_{ori}$), filtered R-wave amplitude ($R_{filt}$), filtered T-wave amplitude ($T_{filt}$), original R-wave amplitude during VT ($VT_{ori}$) or VF, and filtered R-wave amplitude during VT ($VT_{filt}$) or VF to quantify a performance of each of the plurality of filters in accordance with the following equation:

$$\text{score} = w1 \times \frac{R_{filt}}{R_{ori}} + w2 \times \frac{VT_{filt}}{VT_{ori}} + w3 \times \left(1 - \frac{T_{filt}}{R_{filt}}\right)$$

where w1, w2, and w3 are weights.

20. The computer implemented method of claim 13, further comprising periodically analyzing the plurality of filtered signals based on one or more triggering events, wherein the one or more triggering events comprises one or both of a predetermined time period or an R-wave amplitude below a predetermined threshold.

21. The computer implemented method of claim 13, further comprising determining the desired one of the plurality of filters via scoring the plurality of filter signals based on at least: (i) attenuation of R-waves during sinus rhythm (SR) and (ii) attenuation of R-waves during ventricular tachycardia (VT) or ventricular fibrillation (VF).

* * * * *